(12) United States Patent
Oslund et al.

(10) Patent No.: US 10,085,827 B2
(45) Date of Patent: *Oct. 2, 2018

(54) DISTAL PROTECTION DEVICE

(71) Applicant: Covidien LP, Mansfield, MA (US)

(72) Inventors: John Oslund, Cottage Grove, MN (US); Chad Volk, West Fargo, ND (US)

(73) Assignee: Covidien LP, Mansfield, MA (US)

( * ) Notice: Subject to any disclaimer, the term of this patent is extended or adjusted under 35 U.S.C. 154(b) by 629 days.

This patent is subject to a terminal disclaimer.

(21) Appl. No.: 14/684,512

(22) Filed: Apr. 13, 2015

(65) Prior Publication Data

US 2015/0282924 A1 Oct. 8, 2015

Related U.S. Application Data

(60) Continuation of application No. 10/823,139, filed on Apr. 13, 2004, now Pat. No. 9,005,236, which is a division of application No. 09/628,212, filed on Jul. 28, 2000, now Pat. No. 6,740,061.

(51) Int. Cl.
*A61M 29/00* (2006.01)
*A61F 2/01* (2006.01)

(52) U.S. Cl.
CPC ........... *A61F 2/013* (2013.01); *A61F 2/01* (2013.01); *A61F 2002/011* (2013.01); *A61F 2002/018* (2013.01); *A61F 2230/0008* (2013.01); *A61F 2230/008* (2013.01); *A61F 2230/0067* (2013.01)

(58) Field of Classification Search
CPC .............................................. A61F 2002/011
See application file for complete search history.

(56) References Cited

U.S. PATENT DOCUMENTS

| | | |
|---|---|---|
| 4,425,908 A | 1/1984 | Simon |
| 4,662,885 A | 5/1987 | DiPisa, Jr. |
| 5,152,777 A | 10/1992 | Goldberg et al. |
| 5,192,286 A | 3/1993 | Phan et al. |
| 5,329,942 A | 7/1994 | Gunther et al. |
| 5,370,657 A | 12/1994 | Irie |
| 5,375,612 A | 12/1994 | Cottenceau et al. |
| 5,421,832 A | 6/1995 | Lefebvre |
| 5,456,667 A | 10/1995 | Ham et al. |
| 5,531,788 A | 7/1996 | Dibie et al. |
| 5,549,626 A | 8/1996 | Miller et al. |
| 5,556,426 A | 9/1996 | Popadiuk et al. |
| 5,593,442 A | 1/1997 | Klein |

(Continued)

FOREIGN PATENT DOCUMENTS

| | | |
|---|---|---|
| DE | 29916162 U1 | 1/2000 |
| EP | 1127556 A2 | 8/2001 |

(Continued)

OTHER PUBLICATIONS

US 6,348,062, 02/2002, Hopkins et al. (withdrawn)

(Continued)

*Primary Examiner* — Gregory Anderson
(74) *Attorney, Agent, or Firm* — Shumaker & Sieffert, P.A.

(57) ABSTRACT

A distal protection device provided with a filter basket having a self-expanding radial loop designed to position the filter basket within human vasculature and to hold the filter basket open during deployment.

20 Claims, 2 Drawing Sheets

(56) References Cited

U.S. PATENT DOCUMENTS

| | | |
|---|---|---|
| 5,639,277 A | 6/1997 | Mariant et al. |
| 5,649,906 A | 7/1997 | Gory et al. |
| 5,662,671 A | 9/1997 | Barbut et al. |
| 5,669,933 A | 9/1997 | Simon et al. |
| 5,769,816 A | 6/1998 | Barbut et al. |
| 5,776,162 A | 7/1998 | Kleshinski |
| 5,779,716 A | 7/1998 | Cano et al. |
| 5,795,322 A | 8/1998 | Boudewijn |
| 5,800,457 A | 9/1998 | Gelbfish |
| 5,800,525 A | 9/1998 | Bachinski et al. |
| 5,814,064 A | 9/1998 | Daniel et al. |
| 5,820,613 A | 10/1998 | Van Werven-Franssen et al. |
| 5,827,324 A | 10/1998 | Cassell et al. |
| 5,836,969 A | 11/1998 | Kim et al. |
| 5,843,168 A | 12/1998 | Dang |
| 5,846,260 A | 12/1998 | Maahs |
| 5,876,367 A | 3/1999 | Kanganov et al. |
| 5,893,869 A | 4/1999 | Barnhart et al. |
| 5,895,399 A | 4/1999 | Barbut et al. |
| 5,925,062 A | 7/1999 | Purdy |
| 5,935,162 A | 8/1999 | Dang |
| 5,941,896 A | 8/1999 | Kerr |
| 5,947,995 A | 9/1999 | Samuels |
| 5,954,745 A | 9/1999 | Gertler et al. |
| 5,968,071 A | 10/1999 | Chevillon et al. |
| 5,976,172 A | 11/1999 | Homsma et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,007,574 A | 12/1999 | Pulnev et al. |
| 6,010,522 A | 1/2000 | Barbut et al. |
| 6,051,014 A | 4/2000 | Jang |
| 6,053,932 A | 4/2000 | Daniel et al. |
| 6,063,113 A | 5/2000 | Kavteladze et al. |
| 6,068,645 A | 5/2000 | Tu |
| 6,093,199 A | 7/2000 | Brown et al. |
| 6,096,053 A | 8/2000 | Bates |
| 6,129,739 A | 10/2000 | Khosravi |
| 6,142,987 A | 11/2000 | Tsugita |
| 6,146,396 A | 11/2000 | Konya et al. |
| 6,152,946 A * | 11/2000 | Broome .............. A61F 2/01 606/200 |
| 6,152,947 A | 11/2000 | Ambrisco et al. |
| 6,159,165 A | 12/2000 | Ferrara et al. |
| 6,159,230 A | 12/2000 | Samuels |
| 6,168,570 B1 | 1/2001 | Ferrara |
| 6,168,604 B1 | 1/2001 | Cano |
| 6,171,328 B1 | 1/2001 | Addis |
| 6,174,318 B1 | 1/2001 | Bates et al. |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,231,544 B1 | 5/2001 | Tsugita et al. |
| 6,245,087 B1 | 6/2001 | Addis |
| 6,245,089 B1 | 6/2001 | Daniel et al. |
| 6,277,139 B1 | 8/2001 | Levinson et al. |
| 6,325,815 B1 * | 12/2001 | Kusleika .............. A61B 17/221 606/200 |
| 6,344,049 B1 | 2/2002 | Levinson et al. |
| 6,355,051 B1 | 3/2002 | Sisskind et al. |
| 6,364,895 B1 | 4/2002 | Greenhalgh |
| 6,371,970 B1 | 4/2002 | Khosravi et al. |
| 6,468,291 B2 | 10/2002 | Bates et al. |
| 6,511,497 B1 | 1/2003 | Braun et al. |
| 6,540,722 B1 | 4/2003 | Boyle et al. |
| 6,589,263 B1 | 7/2003 | Hopkins et al. |
| 6,610,077 B1 | 8/2003 | Hancock et al. |
| 6,616,680 B1 | 9/2003 | Thielen |
| 6,740,061 B1 | 5/2004 | Oslund et al. |
| 6,755,847 B2 | 6/2004 | Eskuri |
| 6,893,451 B2 | 5/2005 | Cano et al. |
| 2001/0044632 A1 | 11/2001 | Daniel et al. |
| 2002/0022858 A1 | 2/2002 | Demond et al. |
| 2002/0026211 A1 | 2/2002 | Khosravi et al. |
| 2002/0058911 A1 | 5/2002 | Gilson et al. |
| 2003/0120303 A1 | 6/2003 | Boyle et al. |
| 2004/0199203 A1 | 10/2004 | Oslund et al. |

FOREIGN PATENT DOCUMENTS

| | | |
|---|---|---|
| JP | 05212121 A | 8/1993 |
| JP | 7088192 A | 4/1995 |
| JP | 10005343 A | 1/1998 |
| JP | 10174720 A | 6/1998 |
| JP | 10201855 A | 8/1998 |
| JP | 11262531 A | 9/1999 |
| WO | WO 98/01086 A1 | 1/1998 |
| WO | WO 98/39053 A1 | 9/1998 |
| WO | WO 99/09895 A1 | 3/1999 |
| WO | WO 99/23976 A1 | 5/1999 |
| WO | WO 99/42162 A1 | 8/1999 |
| WO | WO 00/16846 A1 | 3/2000 |
| WO | WO 00/67669 A1 | 11/2000 |
| WO | WO 01/03764 A1 | 1/2001 |
| WO | WO 01/08742 A1 | 2/2001 |
| WO | WO 01/08743 A1 | 2/2001 |
| WO | WO 01/87183 A2 | 11/2001 |
| WO | WO 02/11626 A2 | 2/2002 |
| WO | WO 02/11627 A2 | 2/2002 |
| WO | WO 02/054984 A2 | 7/2002 |
| WO | WO 03/059202 A2 | 7/2003 |

OTHER PUBLICATIONS

Partial Search Report from European Patent Application No. 01402012.7, dated Dec. 8, 2003, 5 pp.

Prosecution History from U.S. Appl. No. 10/823,139, dated Sep. 3, 2004 through Dec. 12, 2014, 264 pp.

Supplementary Partial Search Report from counterpart European Patent Application No. 01402012.7, dated Jan. 23, 2004, 6 pp.

Examination Report from European Patent Application No. 01402012.7, dated Oct. 23, 2008, 4 pp.

* cited by examiner

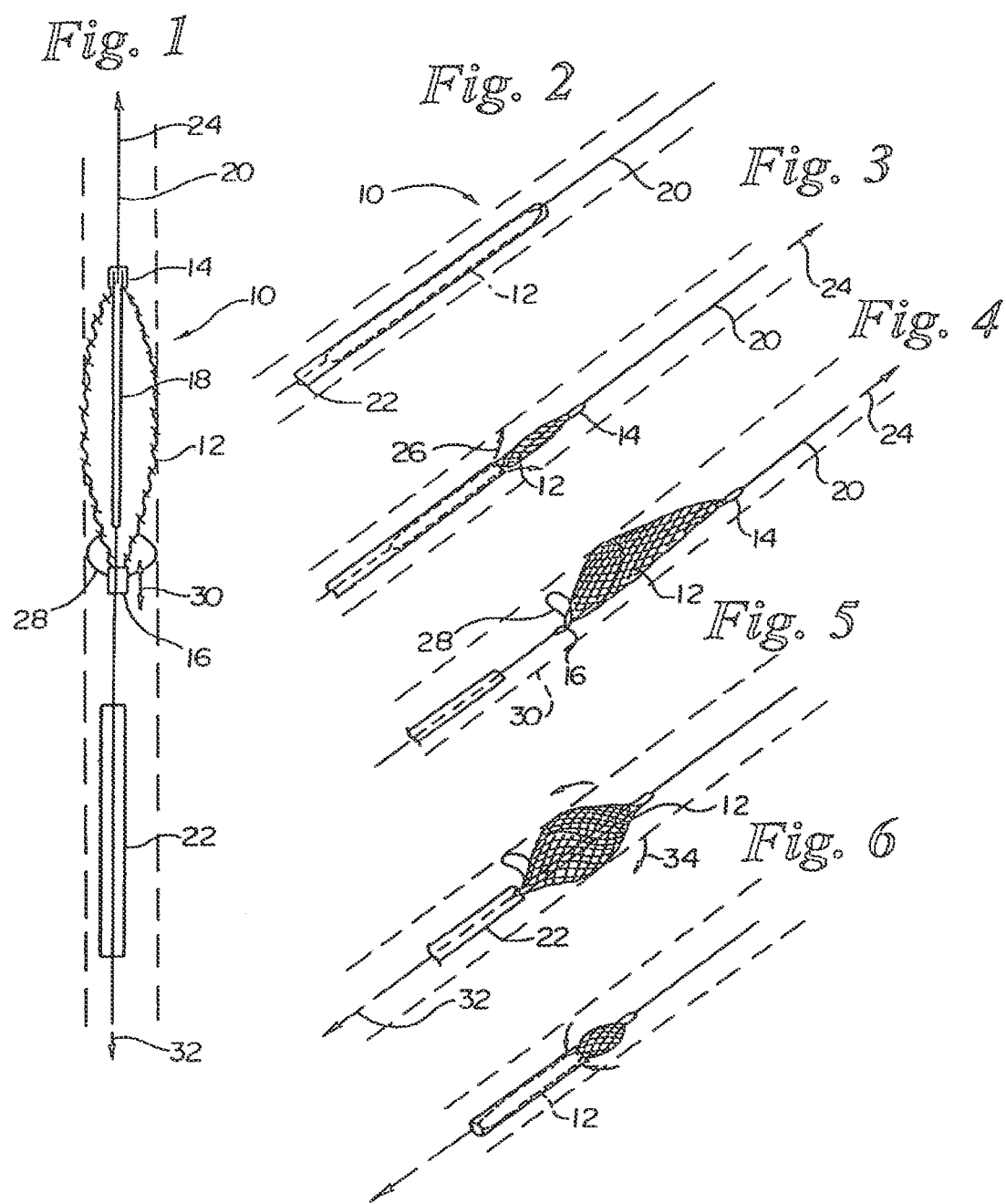

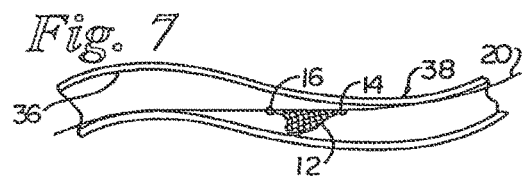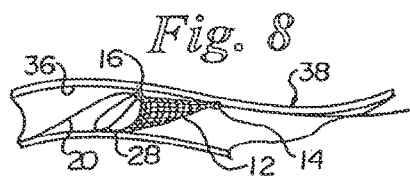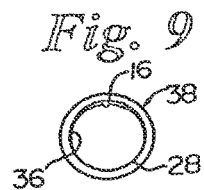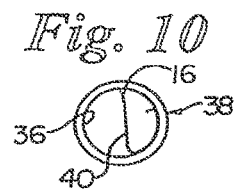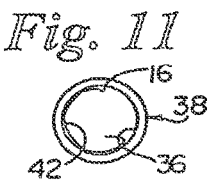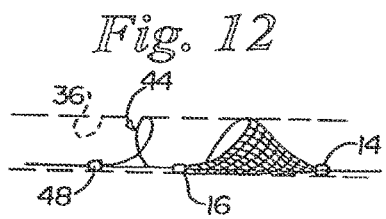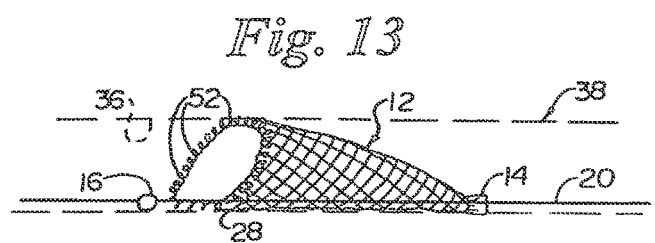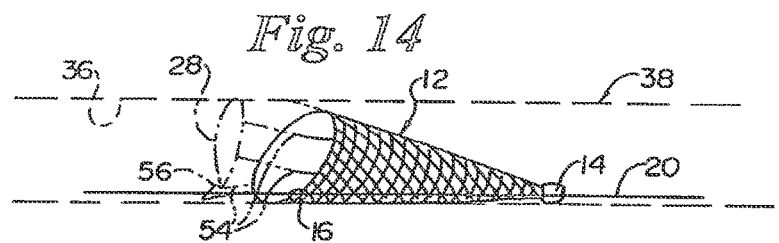

DISTAL PROTECTION DEVICE

CROSS-REFERENCE TO RELATED APPLICATION

This Application is a continuation of U.S. patent application Ser. No. 10/823,139 by Oslund et al., filed on Apr. 13, 2004, which is a division divisional of U.S. patent application Ser. No. 09/628,212, by Oslund et al., filed Jul. 28, 2000, now U.S. Pat. No. 6,740,061. The entire content of both U.S. patent application Ser. Nos. 10/823,139 and 09/628,212 are incorporated herein by reference.

FIELD OF THE INVENTION

The present invention relates to devices deployable in a vessel of the body such as a distal protection device deployable in a blood vessel. In one of its more particular aspects, the invention relates to the positioning of a guidewire or filter within human vasculature.

BACKGROUND OF THE INVENTION

Any intervention into human vasculature can give rise to the need for capturing and retrieving debris, such as grumous matter, emboli, or thrombi, from the affected vessel. Filters of various types have found use, for example, in trapping blood clots and other debris released into the bloodstream. Many filters, however, can be only partially effective in capturing the debris from surgical or catheterization interventions because deployment of the filter within the blood vessel may not provide complete filtration. That is, a filter may not effect filtration across the full cross-section of the blood flow through the vessel. This may result from failing to maintain an optimum fit of the filter within the vessel wall. Where a filter basket is used, another cause for concern is that the basket may not always be fully opened upon deployment within the vessel.

Specifically, filters are traps that have been designed to be used to collect dislodged matter, such as grumous matter, emboli or thrombi, during procedures such as stent installation in coronary saphenous vein grafts. Such filters or traps serve to provide protection from distal embolization that might result in a major adverse coronary event or other acute complication. Embolization of debris which might be released during such procedures and the resulting sequellae have been described in reports documenting major adverse cardiac event rates. Such events include acute myocardial infarction, revascularization and even death.

In order to address such acute embolic-related complications, distal filtration and protection devices have been developed. Such devices have been designed to work with existing interventional modalities. Such devices provide debris-filtering protection during invasive procedures and are intended to prevent complications of particulate embolization.

Such distal filtration and protection devices are typically deployed at a location along a vessel of the body at a desired location. Such deployment is performed by extending the device outwardly from the distal end of a catheter. In order to facilitate deployment, the device to be deployed typically has components made from a shape-memory or highly elastic material. Consequently, they are able to be collapsed within the catheter and, upon being urged outwardly beyond the distal end of the catheter, they reassume their uncollapsed shape.

Nevertheless, performance of such filtration and protection devices is less than perfect. One significant drawback is the general lack of rigidity of the device. While shape-memory materials are used and the device, once released from the catheter, tends to assume an intended uncollapsed configuration, the path of the vessel within which it is intended to be installed can be tortuous. The guidewire upon which the device is installed, therefore, tends to alternately engage opposite sides of the internal vessel wall as the vessel sinuates back and forth. This circumstance can cause the filtration/protection device to become at least partially collapsed between the guidewire and the internal vessel wall. This can result in at least a portion of the mouth of the device being closed and not fully covering the cross-section of the vessel. At least a portion of flow through the vessel can, then, bypass the device.

At least one other circumstance might result in the filtration/protection device becoming at least partially collapsed and a commensurate closure of at least a portion of the mouth of the device. When the guidewire carries a percutaneous transluminal coronary angioplasty (PTCA) balloon, stent or IVUS catheter, the radial position of the guidewire within the internal vessel can be altered from a desired generally central location. When the guidewire is displaced in this manner, the device can become partially collapsed, as discussed above, with commensurate partial or complete closure of the mouth of the device. Again, at least a portion of flow through the vessel can, thereby, bypass the device.

It is to these problems and dictates of the prior art that the present invention is directed. It is an improved distal protection device deployable in a blood vessel which facilitates maximization of desired filtration/protection.

SUMMARY OF THE INVENTION

It is an object of the present invention to provide a distal protection device which can be deployed to fit optimally within a blood vessel or other human vasculature. Another object of this invention is to provide a distal protection device having a filter basket which is maintained in the fully opened configuration after deployment and during use. Other objects and advantages of the present invention will become apparent from the following detailed disclosure and description.

The distal protection device of the present invention is provided with a self-expanding member, shown, in one embodiment, as a loop, that creates a radial force against a vessel wall to control the lateral position of a filter at a desired location in a blood vessel. The self-expanding loop functions to maintain open a proximal opening on a distal protection device such as a filter basket. The loop creates a radial force on the device's guidewire at or near the proximal end of the distal protection device, pushing the guidewire and filter carried by the guidewire against the vessel wall. Any debris formed as a result of proximal intervention, such as by PTCA or stenting, is thereby caused to enter the proximal opening of the basket. Prior to the present invention, the guidewire could be so positioned as to keep the proximal end of the filter basket from opening fully in various tortuous anatomy, resulting in failure to capture debris intended to be captured by the basket.

In one embodiment, the invention includes an element which serves to maintain the filter basket, when deployed, laterally on a defined side of the guidewire. Also included in this embodiment is a collapsible, quasi-rigid loop, or other type of spacer, carried proximate a mouth of the filter basket. The loop or other spacer member is positioned along the guidewire at or proximate the mouth of the filter basket so as to extend laterally on the same side of the guidewire as does the filter basket. Axial alignment of the loop or spacer and filter basket is achieved, in this embodiment, by rigidly fixing the spacer to the element which serves to maintain the filter basket on the defined side of the guidewire, or rigidly fixing the spacer to the guidewire by a separate securing element axially spaced from the filter basket affixation element, but with the spacer axially aligned with the filter basket. It will be understood that the specific loop or other spacer used is provided with a dimension on the side of the guidewire on which it deploys sufficient so as to engage an inner surface of the vessel at a particular circumferential location and, concurrently, urge the guidewire against the inner surface of the vessel at a location generally diametrically opposite that of the location engaged by the spacer.

The self-expanding loop can, as discussed above, be positioned on the guidewire at a location at or proximate the opening of the filter basket or embedded in the braid of the filter basket at or near its proximal end. It will be understood, in view of this disclosure, that the self-expanding loop or other spacer can be made, in one embodiment, to extend on the same lateral side of the guidewire as does the filter basket even when they both rotate concurrently. This can be accomplished by having the spacer attached to an element by which the filter basket is fixed to the guidewire, having the spacer interwoven into the mouth of the filter basket, or having the spacer tethered to the mouth of the filter basket so that, as the filter basket moves rotationally within the vessel of the body, the spacer will commensurately be moved so that substantial axial alignment is maintained.

The loop, while relatively rigid when expanded, is collapsible along with the filter basket for insertion into a delivery catheter. Insertion can be readily accomplished by either front-loading or back-loading. The loop expands upon deployment at a desired treatment location during a medical procedure such as a coronary intervention.

The loop can be constructed in a generally circular shape or can be formed in various "C", "J" or spiral configurations, as desired. A continuous loop is preferred.

The loop may extend generally perpendicular to the guidewire when expanded, since, in that position, it exerts the greatest radial force, being deployed perpendicular to the vessel wall, and provides an optimal fit within the vessel. However, although perpendicular deployment is preferred, an adequate radial force can be generated by expansion of the loop at any angle between 45 degrees and 90 degrees relative to the axis of the guidewire.

The loop can be constructed of a single small diameter wire, such as a nitinol wire, or cable, coil, or stranded cable. It can be radiopaque or covered by a radiopaque material, if desired, to enable the viewing of the proximal opening of the distal protection device when deployed during a procedure.

The present invention is thus an improved apparatus for effecting optimum functioning of a distal protection filter basket. The spacer of the present invention makes it likely that the proximal opening of the distal protection device remains fully open while deployed. It expands and positions itself upon deployment. It does not interfere with the operation of the distal protection device, does not interfere with debris capture, and does not interfere with blood flow.

BRIEF DESCRIPTION OF THE DRAWINGS

FIG. 1 is a plan view, partly in cross section, of one embodiment of the present invention, the inner wall of a blood vessel shown in phantom;

FIG. 2 is a perspective view, partly in cross section, of one embodiment of the present invention, showing the filter basket within a delivery catheter;

FIG. 3 is a view similar to FIG. 2, showing the filter basket partially removed from the catheter;

FIG. 4 is a view similar to FIGS. 2 and 3, showing the filter basket fully removed from the catheter;

FIG. 5 is a view similar to FIGS. 2, 3, and 4, showing the filter basket partially repositioned within the catheter;

FIG. 6 is a view similar to FIGS. 2, 3, 4, and 5, showing the filter basket further repositioned within the catheter;

FIG. 7 is a view similar to FIG. 4 illustrating a distal protection device, not employing the spacer in accordance with the present invention, deployed in a vessel traversing a tortuous course;

FIG. 8 is a view similar to FIG. 7 showing the effects of installing a spacer in accordance with the present invention;

FIG. 9 is a cross-sectional view illustrating the fitting of a loop spacer in a blood vessel;

FIG. 10 is a view similar to FIG. 9 illustrating the installation of a J-shaped spacer;

FIG. 11 is a view similar to FIGS. 9 and 10 illustrating a C-shaped spacer;

FIG. 12 is a view similar to FIG. 8 illustrating the installation of a spiral-shaped spacer;

FIG. 13 is a view similar to FIGS. 8 and 12 illustrating the installation of a continuous loop spacer interwoven into the mouth of the filter basket; and FIG. 14 is a view similar to FIGS. 8, 12 and 13 illustrating the installation of a continuous-loop spacer which is tethered to the mouth of the filter basket.

DETAILED DESCRIPTION OF THE INVENTION

Referring to the drawings, a preferred distal protection device 10 of the present invention is shown in various stages of its use. FIGS. 1 and 4 show device 10 in its fully deployed state. In one embodiment, basket 12, which, as seen in various figures, can be generally in the shape of a windsock, is attached to a guidewire 20, passing through a placement device or stop (i.e., through the lumen of a tube 18), by an element 14 attaching basket 12 to guidewire 20 and holding basket 12 to prevent axial and revolutional movement with respect to guidewire 20. Guidewire 20 is adapted for movement in either the distal direction, shown by arrow 24, or the proximal direction, shown by arrow 32. A ferrule 16 attached at the proximal end of basket 12 can enable movement of the proximal end of basket 12 along guidewire 20 in either the distal or proximal directions, as indicated by arrows 30. When moved in a distal direction, it can, as best seen in FIG. 1, engage stop/tube 18. It will be understood, however, that ferrule 16 can, if desired, be axially fixed on guidewire 20.

A delivery catheter 22 is shown extending in the proximal direction relative to basket 12 with guidewire 20 passing through the lumen of catheter 22. FIG. 4 also shows a spacer or loop 28 attached to the proximal end of basket 12 by means of ferrule 16. In such an embodiment, loop 28, along with basket 12, can concurrently float relative to guidewire 20. When ferrule 16 serves as an element to lock loop 28 with respect to the mouth of basket 12, loop 28 is positioned so that it is substantially axially aligned with the mouth of the basket 12. Because of the quasi-rigid nature of loop 28, it will have the effect of urging ferrule 16 and guidewire 20 against inner wall 36 of the vessel 38. Radial expansion of loop 28 will facilitate maintenance of the mouth of basket 12 fully opened.

It will be understood that, in certain embodiments, a separate element (not shown in the figures) could be used to maintain loop 28 proximate the proximal end of basket 12 and lock loop 28 in general axial alignment with basket 12. When such a separate element is used, however, it would function to maintain loop 28 at a location about guidewire 20 so that loop 28 is generally axially aligned with basket 12. Such embodiments can permit positioning of loop 28 at a location proximally spaced from ferrule 16. Such spacing will enable the vessel of the body in which the basket 12 is deployed to taper to a normal diameter if the loop 28 has caused expansion.

Also contemplated by the invention are embodiments illustrated in FIGS. 13 and 14. FIG. 13 illustrates a filter basket 12 wherein the mouth of the basket is, in fact, defined by the loop 28. In this embodiment, strands of the basket mesh 52 are interwoven about loop 28 to effectively integrate the loop 28 and basket 12. As loop 28 engages inner wall 36 of vessel 38, the mouth of the basket, commensurately, occupies substantially the full cross-section of vessel 38.

FIG. 14 illustrates a basket 12 secured to guidewire 20 by means as previously discussed. Loop 28 is shown as being secured to guidewire 20 by an element 56 spaced axially along guidewire 20 from the proximal end or mouth of basket 12. In this embodiment, element 56 may permit loop 28 to revolve about guidewire 20 independently of basket 12. Tethers 54 are, however, employed to maintain a substantial axial alignment of loop 28 with the mouth of filter basket 12.

As will be seen, the invention contemplates a number of methods of maintaining a desired relationship between the spacer and the filter basket 12. What is significant, of course, is that there be a general axial alignment maintained between the two.

Referring now to FIG. 2, basket 12 is shown completely enclosed within catheter 22. In FIG. 3 movement of guidewire 20 in the distal direction, indicated by arrow 24, partially removes basket 12 from catheter 22 as shown by arrows 26. In FIGS. 5 and 6 arrows 34 show partial retraction of basket 12 and loop 28 into catheter 22 by movement of guidewire 20 in the proximal direction indicated by arrow 32.

FIG. 7 illustrates a distal protection device basket 12 attached to a guidewire 20 extending through a tortuous path of a blood vessel. The device illustrated in FIG. 7 is secured to guidewire 20 by means of element 14 and ferrule 16, as was described with regard to FIGS. 1-6. In FIG. 7, however, a consequence of traversing the tortuous path of a blood vessel is illustrated. As seen, the guidewire 20 will tend to take the most direct route through the vessel and, alternatively, engage generally diametrically opposite sides of the inner wall 36 of the vessel 38. As will be able to be seen in viewing FIG. 7, the filter basket 12 can become partially collapsed between the run of the guidewire 20 and the inner wall 36 of the vessel 38. The possibility would then exist that debris in the stream of flow could bypass the filter basket 12.

FIG. 8 illustrates how use of a loop spacer 28 in accordance with the present invention overcomes this problem. Loop 28 is fixedly attached to element or ferrule 16 so that it will be maintained on the same side of guidewire 20 on which filter basket 12 is maintained. Because of the quasi-rigid nature of the loop 28, when it is deployed from catheter 22 it will engage a circumferential point on the inner wall 36 of the vessel 38 generally diametrically opposite the point of connection at ferrule 16. The rigidity of loop 28 will effectively urge guidewire 20 against a circumferential point of inner wall 36, opposite the location of engagement of the wall by the point of loop 28, distal with respect to the point of loop 28 (that is, at ferrule 16). In consequence, filter basket 12 will be enabled to fully expand and, thereby, afford maximum protection.

FIG. 9 illustrates, in cross-section, the functioning of loop spacer 28 with respect to inner wall 36 of vessel 38. FIGS. 10 and 11 show alternative embodiments of the spacer. FIG. 10 illustrates a generally J-shaped spacer 40. FIG. 11 illustrates a generally C-shaped spacer 42. As will be able to be seen in view of this disclosure, in both of these alternative embodiments, ferrule 16 and guidewire 20 will be driven against inner wall 36 of vessel 38 at a circumferential location generally opposite the location at which the spacer engages the wall 36. As a result, operation of the filter basket 12 will be maximized.

FIG. 12 illustrates the functioning of a spiral-shaped spacer 44. Spiral-shaped spacer 44 is shown as being connected, at a distal end thereof, to ferrule 16. Such a connection would be substantially rigid so that the orientation of spacer 44 would be at a location so as to be generally axially aligned with the mouth of basket 12. While, in embodiments wherein ferrule 16 can float axially, spacer 44 will commensurately be allowed to float axially, it will nevertheless be maintained revolutionally about guidewire 20 so as to afford the desired axial alignment with basket 12.

FIG. 12 also illustrates another ferrule 48 which maintains the proximal end of spacer 44 at guidewire 20. It will be understood that this ferrule 48 may be permitted to float in an axial direction also or be fixedly attached at guidewire 20.

It will be understood that spiral spacer 44 in FIG. 12 can also be maintained, as is true in the case of other embodiments, rigidly with respect to guidewire 20 by elements separate from ferrule 16. In such a case, this can be accomplished by rigidly securing the independent elements to the guidewire 20 or additionally, for example, tethering spacer 44 to the mouth of the filter basket 28.

Other embodiments of the spacer are also specifically contemplated. For example, a continuous loop bent back on itself in a J-shape or C-shape are also intended to be encompassed within the invention. These particular embodiments are not illustrated in the drawing figures.

Although a preferred embodiment has been described, it will be appreciated that the description and disclosure in the instant specification are set forth by way of illustration and not limitation, and that various modifications and changes may be made without departing from the spirit and scope of the present invention. Other embodiments can also be used to effect the objects of this invention.

What is claimed is:

1. A device comprising:
   a guidewire;
   a filter basket connected to the guidewire, the filter basket comprising a closed distal end and an open proximal end, the distal end fixedly secured to the guidewire and the proximal end moveable along the guidewire; and
   a spacing member connected to the guidewire and positioned proximate to the proximal end of the filter basket.

2. The device of claim 1, further comprising a tube surrounding the guidewire and positioned within the filter basket, the tube being configured for axial movement along the guidewire.

3. The device of claim 2, wherein distal movement of the proximal end of the filter basket along the guidewire is limited by a proximal end of the tube.

4. The device of claim 1, wherein the spacing member is self-expanding.

5. The device of claim 4, wherein the spacing member is configured to expand independent of the proximal end of the filter basket.

6. The device of claim 1, further comprising a ferrule, wherein the spacing member and the proximal end of the filter basket are connected to the ferrule, the ferrule connecting the spacing member to the guidewire.

7. The device of claim 6, wherein the ferrule is movable relative to the guidewire.

8. The device of claim 1, further comprising a stop, wherein distal movement of the proximal end of the filter basket is limited by the stop.

9. The device of claim 1, wherein the spacing member defines a loop, and wherein the device further comprises at least one axially extending tether, the tether connecting a point on the spacing member to a corresponding point on the proximal end of the filter basket.

10. A method comprising:
    inserting a catheter containing a distal protection device in a collapsed configuration into a vessel of a patient, wherein the distal protection device comprises:
        a guidewire;
        a filter basket connected to the guidewire, the filter basket comprising a closed distal end and an open proximal end, the distal end fixedly secured to the guidewire and the proximal end moveable along the guidewire; and
        a spacing member connected to the guidewire and positioned proximate to the proximal end of the filter basket; and
    deploying the distal protection device within the vessel.

11. The method of claim 10, wherein deploying the distal protection device comprises deploying the distal protection device on a side of the vessel distal to a location affected by a medical procedure.

12. The method of claim 10, wherein deploying the distal protection device comprises advancing the filter basket distal to the catheter, wherein the spacing member is self-expanding.

13. The method of claim 10, further comprising:
    maintaining a position of the distal protection device within the vessel during a medical procedure; and
    capturing, with the filter basket, debris produced by the medical procedure.

14. The method of claim 13, further comprising repositioning the filter basket within the catheter after completion of the medical procedure.

15. A device comprising:
    a guidewire;
    a filter basket connected to the guidewire, the filter basket comprising a closed distal end and an open proximal end, the distal end fixedly secured to the guidewire and the proximal end moveable along the guidewire; and
    a spacing member comprising an arcuate wire extending from a proximal end to a distal end, the distal end of the arcuate wire connected to at least one of the proximal end of the filter basket or the guidewire, the spacing member being configured to urge the guidewire toward an inner surface of a vessel in a patient.

16. The device of claim 15, wherein the proximal end of arcuate wire is connected to the guidewire, the arcuate wire forming a loop.

17. The device of claim 15, wherein the proximal end of arcuate wire is connected to the guidewire at a position proximal to the proximal end of the filter basket.

18. The device of claim 15, wherein the arcuate wire forms a C-shaped or J-shaped curve.

19. The device of claim 15, further comprising a ferrule, the ferrule connecting the distal end of the arcuate wire to the proximal end of the filter basket and the guidewire.

20. The device of claim 19, wherein the ferrule is movable in an axial direction relative to the guidewire.

* * * * *